(12) United States Patent
Grado et al.

(10) Patent No.: US 12,214,201 B2
(45) Date of Patent: Feb. 4, 2025

(54) METHOD FOR ADAPTIVE CONTROL OF A MEDICAL DEVICE USING BAYESIAN OPTIMIZATION

(71) Applicant: REGENTS OF THE UNIVERSITY OF MINNESOTA, Minneapolis, MN (US)

(72) Inventors: Logan Grado, Minneapolis, MN (US); Theoden Netoff, Minneapolis, MN (US); Andy Lamperski, Minneapolis, MN (US); Bryan Moore, Minneapolis, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 135 days.

(21) Appl. No.: 16/966,390

(22) PCT Filed: Feb. 1, 2019

(86) PCT No.: PCT/US2019/016380
§ 371 (c)(1),
(2) Date: Jul. 30, 2020

(87) PCT Pub. No.: WO2019/152858
PCT Pub. Date: Aug. 8, 2019

(65) Prior Publication Data
US 2020/0391037 A1 Dec. 17, 2020

Related U.S. Application Data

(60) Provisional application No. 62/625,134, filed on Feb. 1, 2018.

(51) Int. Cl.
*A61N 1/36* (2006.01)
*A61N 1/365* (2006.01)

(52) U.S. Cl.
CPC ..... *A61N 1/36139* (2013.01); *A61N 1/36132* (2013.01); *A61N 1/36557* (2013.01); *A61N 1/36585* (2013.01)

(58) Field of Classification Search
CPC ............ A61N 1/36585; A61N 1/36557; A61N 1/36132; A61N 1/36139
See application file for complete search history.

(56) References Cited

U.S. PATENT DOCUMENTS 6,345,128 B1   2/2002   Stokes
7,324,851 B1   1/2008   DiLorenzo
(Continued)

FOREIGN PATENT DOCUMENTS

AU   2019200482 A1   2/2019
WO   2014149536 A2   9/2014
(Continued)

OTHER PUBLICATIONS

Azodi-Avval R, et al. Phase-dependent modulation as a novel approach for therapeutic brain stimulation. Frontiers In Computational Neuroscience. Feb. 9, 2015:1-7.
(Continued)

*Primary Examiner* — Alyssa M Alter
(74) *Attorney, Agent, or Firm* — QUARLES & BRADY LLP

(57) ABSTRACT

Systems and methods for adaptively controlling an electrical stimulation device, such as a closed-loop stimulation device, based in part on a Bayesian optimization of the operational parameters of the device are described. An adaptive dual control of the stimulation device can be provided. In a first control loop parameters are extracted from signals recorded from the subject by the stimulation device, and in a second control loop a Bayesian optimization is implemented with a hardware processor and memory to compute updated opera-
(Continued)

tional parameters for the stimulation device. As noted, the stimulation device is an electrical stimulation device, and may be a closed-loop stimulation device. Such devices can be used for deep brain stimulation ("DBS"), cardiac resynchronization therapy ("CRT"), and other electrophysiological stimulation applications.

8 Claims, 10 Drawing Sheets

(56) References Cited

U.S. PATENT DOCUMENTS

| | | | |
|---|---|---|---|
| 9,084,066 | B2 | 7/2015 | De Vries |
| 9,992,586 | B2 | 6/2018 | Nielsen |
| 2010/0008526 | A1 | 1/2010 | De Vries |
| 2011/0178789 | A1 | 7/2011 | Miranda |
| 2014/0081350 | A1 | 3/2014 | Zhu |
| 2015/0190100 | A1 | 7/2015 | Fox |
| 2015/0320588 | A1* | 11/2015 | Connor ............... A61F 7/0085 607/104 |
| 2017/0257713 | A1 | 9/2017 | Westermann |
| 2018/0365194 | A1 | 12/2018 | Grado |

FOREIGN PATENT DOCUMENTS

| | | | | |
|---|---|---|---|---|
| WO | WO-2016134212 | A1 * | 8/2016 | ............ A61B 5/125 |
| WO | 2016205231 | A1 | 12/2016 | |

OTHER PUBLICATIONS

Brochu E, et al. A Tutorial on Bayesian Optimization of Expensive Cost Functions, with Application to Active User Modeling and Hierarchical Reinforcement Learning. arXiv. 2010.
Cagnan H, et al. Stimulating at the right time: phase-specific deep brain stimulation. Brain. 2016; p. 1-14.
Connolly AT, et al. Modulations in Oscillatory Frequency and Coupling in Globus Pallidus with Increasing Parkinsonian Severity. Journal of Neuroscience. 2015; 35(15):6231-6240.
Contarino MF, et al. Directional steering: A novel approach to deep brain stimulation. Neurology. 2014; 83(13):1163-1169.
Courtemanche R, et al. Synchronous, focally modulated beta-band oscillations characterize local field potential activity in the striatum of awake behaving monkeys. The Journal of neuroscience: the official journal of the Society for Neuroscience. 2003; 23(37):11741-11752.
De Hemptinne C, et al. Exaggerated phase-amplitude coupling in the primary motor cortex in Parkinson disease. Proceedings of the National Academy of Sciences of the United States of America. 2013; 110(12):4780-5.
Grado LL, et al. (Dec. 2018) Bayesian adaptive dual control of deep brain stimulation in a computational model of Parkinson's disease. PLoS Comput Biol 14(12):e1006606.
Grado LL, et al. The Sliding Windowed Infinite Fourier Transform. IEEE Signal Processing Magazine. 2017; 34(5):183-188.
Holt AB, et al. Phasic Burst Stimulation: A Closed-Loop Approach to Tuning Deep Brain Stimulation Parameters for Parkinson's Disease. PLoS Computational Biology. 2016; 12(7):1-14.
International Searching Authority. International Search Report and Written Opinion for application PCT/US2019/016380. Mailed on Apr. 30, 2019.
Jackson JC, et al. Computationally efficient, configurable, causal, real-time phase detection applied to local field potential oscillations. In: IEEE EMBS Conference on Neural Engineering; 2015. p. 942-947.
Jensen, B. S., et al. "Efficient preference learning with pairwise continuous observations and Gaussian processes." 2011 IEEE International Workshop on Machine Learning for Signal Processing. IEEE, 2011.
Jensen, B. S., et al. "Pairwise Judgements and Absolute Ratings with Gaussian Process Priors." (2014). Technical University of Denmark.
Little S, et al. Adaptive deep brain stimulation in advanced Parkinson disease. Annals of Neurology. 2013; p. 449-457.
Little S, et al. Bilateral adaptive deep brain stimulation is effective in Parkinson's disease. Journal of Neurology, Neurosurgery & Psychiatry. 2015; p. 717-721.
Locatelli M. Bayesian algorithms for one-dimensional global optimization. J Global Optim. 1997; 10 (1):57-76.
Martinez-Cantin R, et al. A Bayesian exploration-exploitation approach for optimal online sensing and planning with a visually guided mobile robot. Autonomous Robots. 2009; 27(2):93-103.
Mockus J, et al. The application of Bayesian methods for seeking the extremum. Towards Global Optimisation. 1978; 2:117-129.
Mockus J. Application of Bayesian approach to numerical methods of global and stochastic optimization. Journal of Global Optimization. 1994; 4(4):347-365.
Nelder JA, et al. A simplex method for function minimization. The Computer Journal. 1965; 7 (4):308-313.
Nielsen, JBB, et al. "Efficient individualization of hearing aid processed sound." 2013 IEEE International Conference on Acoustics, Speech and Signal Processing. IEEE, 2013.
Nielsen, JBB, et al. "Perception-based personalization of hearing aids using Gaussian processes and active learning." IEEE/ACM Transactions on Audio, Speech, and Language Processing 23.1 (2014): 162-173.
Ryapolova-Webb E, et al. Chronic cortical and electromyographic recordings from a fully implantable device: preclinical experience in a nonhuman primate. Journal of neural engineering. 2014; 11(1):016009.
Santaniello S, et al. Closed-loop control of deep brain stimulation: a simulation study. IEEE Trans Neural Syst Rehabil Eng. 2011; 19(1):15-24.
Smeal RM, et al. Phase-response curves and synchronized neural networks. Philosophical Transactions of the Royal Society B: Biological Sciences. 2010; 365(1551):2407-2422.
Snoek J, et al. Scalable Bayesian Optimization Using Deep Neural Networks. arXiv. 2015.
Springenberg JT, et al. Bayesian Optimization with Robust Bayesian Neural Networks. Nips. 2016; p. 4134-4142.
Srinivas N, et al. Gaussian Process Optimization in the Bandit Setting: No Regret and Experimental Design. arXiv. 2009.
Streltsov S, et al. A Non-myopic Utility Function for Statistical Global Optimization Algorithms. Journal of Global Optimization. 1999; 14(3):283-298.
Volkmann J, et al. Introduction to the programming of deep brain stimulators. Movement disorders: official journal of the Movement Disorder Society. 2002; 17 Suppl 3:S181-7.
European Patent Office. Extended European Search Report for application 19747327.5. Mailed on Oct. 7, 2021. 9 pages.

* cited by examiner

METHOD FOR ADAPTIVE CONTROL OF A MEDICAL DEVICE USING BAYESIAN OPTIMIZATION

CROSS-REFERENCE TO RELATED APPLICATIONS

This application represents the U.S. National Stage of International Application No. PCT/US2019/016380, filed Feb. 1, 2019 which claims the benefit of U.S. Provisional Patent Application Ser. No. 62/625,134, filed on Feb. 1, 2018, and entitled "METHOD FOR ADAPTIVE CONTROL OF A MEDICAL DEVICE USING BAYESIAN OPTIMIZATION," which is herein incorporated by reference in its entirety.

STATEMENT REGARDING FEDERALLY SPONSORED RESEARCH

This invention was made with government support under DGE-1069104 and CMMI-1634445 awarded by National Science Foundation; and NS094206 and NS098573 awarded by National Institutes of Health. The government has certain rights in the invention.

BACKGROUND

Controllable medical devices include electrical stimulation devices for delivering stimulation to patients for treatment, drug pumps for delivering pharmaceutical and other chemical agents to patients, hearing aids, and so on. There exists some level of uncertainty in all control problems. For instance, the parameters of the process may vary, or even the process itself may vary. As one method for handling these uncertainties an adaptive dual controller can be used.

Adaptive dual controllers can help handle process variation by attempting to estimate or identify the unknown parameters of the process, and thus tune the parameters of the feedback controller accordingly. In order to obtain good process information, the process should be perturbed and how the process responds should be learned.

Conversely, the goal of a closed-loop controller is that the output should vary as little as possible. Thus, there is a conflict between information gathering and control. Therefore, in controlling an unknown process, a controller has dual goals. On the one hand, the controller should control the process as well as possible, and on the other hand, the controller should perturb the process in order to gain more information, leading to better control in the future. This compromise between probing and control leads to the concept of dual control.

Programming controllable medical devices, such as electrical stimulation devices is difficult and time consuming. Controllable medical devices often operation based on patient feedback; however, patient symptoms will often fluctuate depending on numerous different factors (e.g., sleep, attention, stress, cognitive and motor load, current drug therapy, patient preference to a treatment), and so the need for updated control of the medical device changes from moment to moment.

Current controllable medical device technologies do not readily adapt to the changing needs of patients. Once the clinician sets the parameters for the controllable medical device, they do not change until the next programming visit. Implantable devices have recently been developed that can simultaneously deliver stimulus and record the neural or other physiological responses, opening the door to adaptive therapies.

Thus, there remains a need to provide an adaptive controller that is capable of controlling a controllable medical device in real-time with automatic tuning of the control parameter settings that accounts for feedback from the patient, including patient preference.

SUMMARY OF THE DISCLOSURE

The present disclosure addresses the aforementioned drawbacks by providing an adaptive controller for controlling a controllable medical device, such as an electrical stimulation device, a drug pump, a hearing aid, or so on. The adaptive dual includes an input, a processor in communication with the input, a memory in communication with the processor, and an output in communication with the processor. The input receives feedback data representative of a treatment response or effect in a subject. The processor is programmed to receive the feedback data from the input and generate a posterior distribution therefrom, to estimate an acquisition function from the posterior distribution, and to generate updated control parameter settings based on the acquisition function. The memory stores instructions for implementing the Bayesian optimization algorithm that generates the updated control parameter settings, the feedback data received from the input, and the updated control parameter settings generated by the processor. The output communicates the updated control parameter settings to a controllable medical device.

It is another aspect of the present disclosure to provide a method for controlling a closed-loop stimulation system having one or more electrodes configured to apply stimulating electrical signals and to receive electrophysiological signals. The method includes measuring, with the one or more electrodes of the closed-loop stimulation system, electrophysiological signals from a subject. A biomarker is estimated from the electrophysiological signals. Electrical stimulation settings are determined based on a Bayesian optimization to which the biomarker is input. The closed-loop stimulation system is then controlled based on the determined electrical stimulation settings.

It is another aspect of the present disclosure to provide a closed-loop stimulation system that includes one or more electrodes configured to apply stimulating electrical signals and to receive electrophysiological signals, and a controller. The controller is configured to measure electrophysiological signals received at the one or more electrodes; estimate at least one of amplitude data or phase data from the measured electrophysiological signals; determine electrical stimulation settings based on a Bayesian optimization to which the at least one of amplitude data or phase data are input; and apply electrical stimulation based on the determined electrical stimulation settings using the one or more electrodes.

It is another aspect of the present disclosure to provide a closed-loop system that includes a parameterized medical device and a controller. The controller is configured to receive biomarker signals from the subject in the form of electrical signals, biophysical feedback measures, ratings, preference, and so on. The controller uses Bayesian optimization to control the parameters of the device in order to iteratively tune the parameters to fit the subject.

The foregoing and other aspects and advantages of the present disclosure will appear from the following description. In the description, reference is made to the accompanying drawings that form a part hereof, and in which there is shown by way of illustration a preferred embodiment. This embodiment does not necessarily represent the full scope of the invention, however, and reference is therefore made to the claims and herein for interpreting the scope of the invention.

DETAILED DESCRIPTION

Described here are systems and methods for adaptively controlling a medical device based in part on a Bayesian optimization of the control parameters of the device. The Bayesian optimization provides automatic tuning of the control parameters of the medical device based on feedback data, such as user response data, to achieve a user-specific therapy or effect. Examples of medical devices that can be adaptively controlled in the manner include electrical stimulation devices, such as peripheral nerve stimulators, central nervous system stimulators, cardiac pacemakers, and cardiac resynchronization therapy ("CRT") devices; drug pumps; hearing aids; cochlear implants; and other such devices with controllable parameters. Examples of feedback data that can be input to the Bayesian optimization include physiological data, such as neural signals, cardiac signals, and chemical signals (e.g., insulin levels, glucose levels). The feedback data may also include behavioral metrics and user preferences (e.g., preferences based on a questionnaire or between two presented options). To implement user preferences, the user preferences can be made into a response surface using a probit function or other suitable statistical or mathematical model.

As one non-limiting example, an adaptive control of the medical device can be provided. Feedback data can be measured or otherwise provided to a controller, and a Bayesian optimization is implemented with a hardware processor and memory to compute updated control parameters for the medical device based in part on the feedback data.

Figure 1:
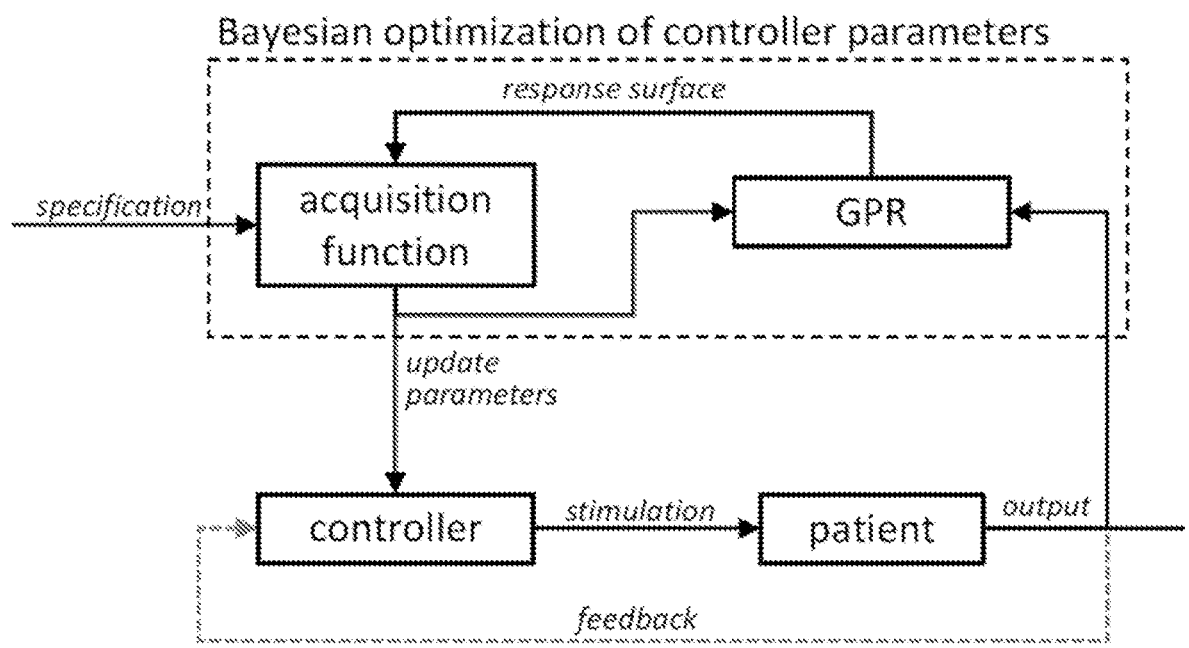
FIG. 1 is a block diagram of an example adaptive control that implements a Bayesian optimization loop for controlling a controllable medical device.

An adaptive controller for use in medical devices is described in the present disclosure. The adaptive controller is implemented using a hardware processor and memory and generally includes a feedback driven control parameter optimization, as shown in FIG. 1.

The feedback driven control parameter optimization of the adaptive controller employs Bayesian optimization to intelligently sample the parameter space and select the optimal set of parameters. In some implementations, the optimization generally operates on a timescale that is on the order of a few seconds, but in some other implementations may operate on longer timescales (e.g., days to weeks). After selecting a new control parameter set, the optimization can wait a delay time in order to allow the subject to settle into a steady state. As an example, the delay time can be on the order of 10 seconds. In some embodiments, the optimization can then estimate one or more measurement parameters from the subject. As one non-limiting example, in DBS applications the optimization can estimate the amplitude of the beta oscillations, or other neuronal signals, over a measurement time. For instance, the amplitude can be estimated by keeping a running average of the oscillations amplitude. The measurement time can be on the order of 10 seconds as well.

Bayesian optimization is well-suited for selecting the optimal parameters of a controllable medical device, such as an electrical stimulation device, drug pump, or hearing aid. For instance, Bayesian optimization offers advantages because direct access to the objective function is often not available for such devices and, thus, noisy observations are made instead; the objective function is expensive to evaluate; there is no access to derivatives; and the optimization problem is not necessarily convex.

In the case of electrical stimulation, the objective function is the user's response to a set of feedback stimulator parameters. It may take seconds, minutes, hours, or even days to obtain a good (likely noisy) measure of the effect of a parameter set. Additionally, in DBS and other electrical stimulation applications there is typically no access to derivatives, and so gradient descent methods cannot be used, and the problem at hand cannot be assumed to be convex, so a global exploration is preferred.

Bayesian optimization address each of these challenges. The Bayesian optimization algorithm generally includes treating the unknown objective function as a random function over which a prior is placed. The prior generally represents the believed behavior of the unknown objective function. This prior is updated based in part on feedback data that are representative of evaluations of the unknown objective function to form a posterior distribution over the unknown objective function. The posterior distribution is then used to generate an acquisition function, which models the utility of sampling across the space. The acquisition function is used to determine the next sample points. As one non-limiting example, the posterior distribution can be a Gaussian process regressor ("GPR") that estimates the objective function with a response surface, and the acquisition function predicts the utility of sampling by incorporating the mean and variance of the GPR.

A Gaussian process is an extension of the multivariate Gaussian distribution to an infinite-dimension stochastic process. A Gaussian process can be thought of as a distribution over functions, specified by a mean function, m, and covariance function (also known as the kernel), k:

$$f(x) \sim GP(m(x), k(x, x')) \quad (1).$$

The prior mean is often assumed to be the zero function $m(x)=0$, or the mean of the training data, $m(x)=\bar{f}$. One example choice is the squared exponential function, $$k(x_i, x_j) = \sigma^2 \exp\left(-\frac{\|x_i - x_j\|^2}{2\ell}\right); \quad (2)$$

where $\sigma^2$ is the variance and $\ell$ is a length scale parameter. In the Bayesian optimization task, the GP is fit to previous observations, $D_{1:n} = \{x_{i:n}, f_{i:n}\}$, in order to obtain the posterior for any point $x_{n+1}$. The predictive distribution can be derived as, $$P(f_{n+1}|D_{1:n}, x_{n+1}) = N(\mu_n(x_{n+1}), \sigma^2(x_{n+1})) \quad (3);$$

where $$\mu_n(x_{n+1}) = k^T K^{-1} f_{1:n} \quad (4);$$

$$\sigma_n^2(x_{n+1}) = k(x_{t+1}, x_{t+1}) - k^T K^{-1} k \quad (5).$$

Thus, given a set of previous observations, D, the mean and variance of any point $x_{n+1}$ can be predicted, which can be used to determine which point should be sampled next using the acquisition function.

The acquisition function, u( . . . ), serves to guide the search to the optimum by modeling the expected utility of sampling at any point, $x_{n+1}$. An acquisition function such as the Gaussian process lower confidence bound ("GP-LCB") function achieves low values in regions where either the prediction is low, the uncertainty is high, or both.

$$GP\text{-}LCB(x) = \mu(x) - \kappa\sigma(x) \quad (6);$$

where $\kappa \geq 0$. Other acquisition functions can also be used. The Bayesian optimization algorithm thus selects the next evaluation point, $x_{n+1}$, by minimizing the acquisition function, such as by sampling at $\operatorname{argmax}_x u(x|D)$.

The acquisition function also governs the trade-off between exploration and exploitation. In GP-LCB, the $\kappa$ parameter determines the exploration-exploitation trade-off, where high values of $\kappa$ encourage exploration and low values of $\kappa$ encourage exploitation.

Figure 2:
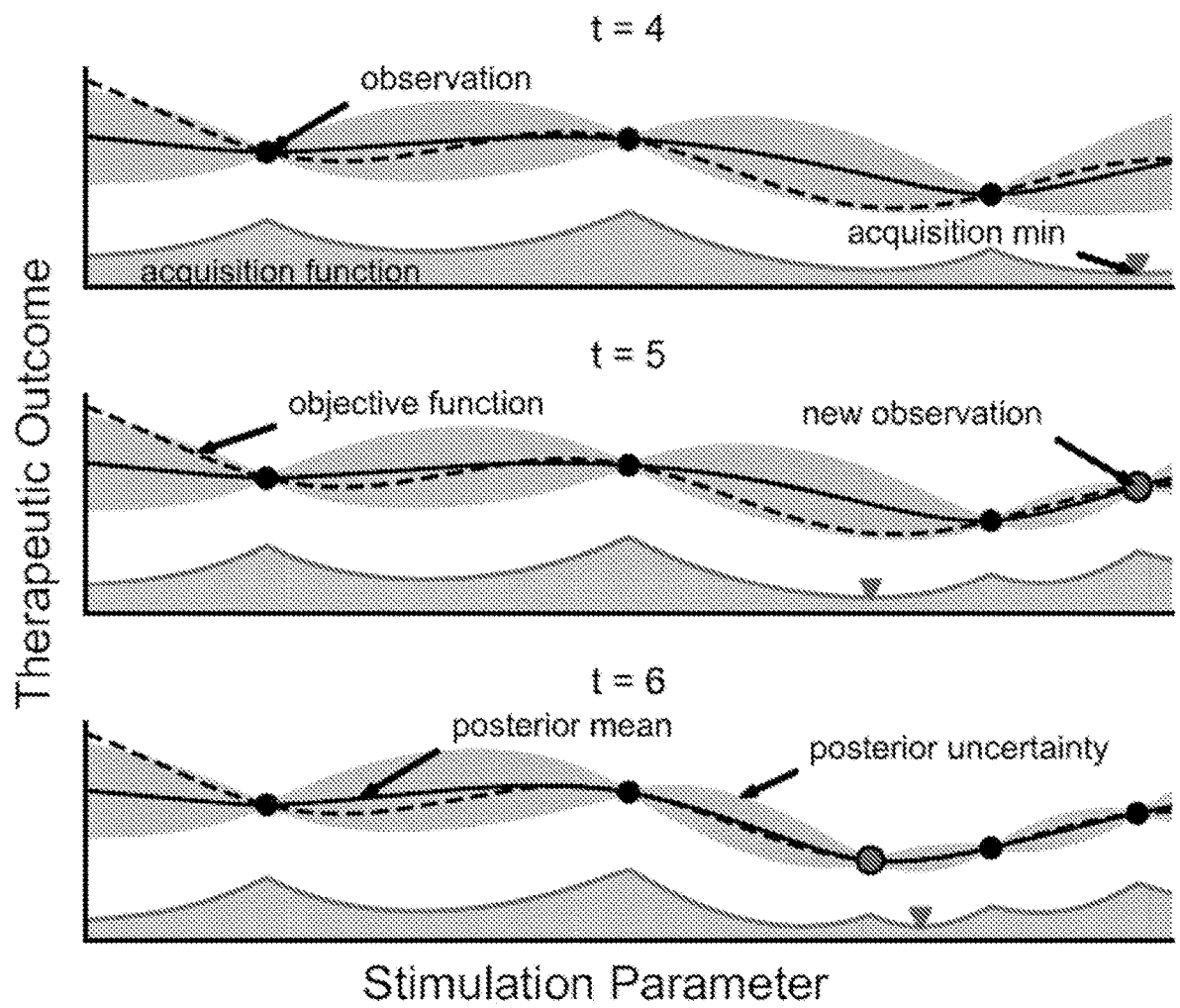
FIG. 2 shows three iterations of Bayesian optimization minimizing a toy 1D problem. The figure shows a Gaussian process (GP) approximation (solid black line) of the underlying objective function (dotted black line), as well as the 95% confidence interval (blue shaded region). The figure also shows the acquisition function (green). The acquisition function (GP-LCB) is the sum of the mean and variance of the GP (multiplied by a constant), which Bayesian optimization uses to determine where to sample next.

With, $$\kappa_t = \sqrt{v\tau_t},$$

$$v = 1, \text{ and}$$

$$\tau_t = 2\log\left(\frac{t^{\frac{d}{2}+2}\pi^2}{3\delta}\right),$$

it can be shown that this method is no regret with high probability. FIG. 2 shows an example run of a Bayesian optimization algorithm on a 1D problem. The optimization starts with 3 points, from which it fits a Gaussian process regressor. The Bayesian optimization algorithm then computes an acquisition function from the GPR, which incorporates both the mean and variance of the GPR, to model the utility of sampling. The Bayesian optimization then minimizes the acquisition function to determine where to sample next. Finally, the objective function is sampled, and the process is repeated. It will be appreciated by those skilled in the art that other forms of Bayesian optimization (e.g., different Bayesian models, different acquisition functions) other than those described here can also be implemented with the systems and methods described in the present disclosure.

In general, feedback data provided to the adaptive controller can be used to generate the response surface estimated by the GPR. As noted above, the feedback data can include physiological feedback data measured from the user, which may include electrophysiological signals, chemical signals, and so on. Such physiological feedback data can be measured by the controllable medical device, or can be provided to the controllable medical device via an input. For instance, the physiological feedback data could be measured by a different medical device and transmitted over a wired or wireless connection to the adaptive controller used for the controllable medical device.

As mentioned above, in some embodiments, the feedback data can include behavioral or user preference data that can be quantified and provided as an additional input to the Bayesian optimization. For instance, the user can qualitatively describe their interpretation of whether a current batch of settings for the controllable medical device are effective or not. As one example, the user preference data can be recorded as responses to a questionnaire. This qualitative feedback can be used to build out a Gaussian process to be used in the Bayesian optimization. As one example, a probit function may be used to build the GPR. A probit function may be, for instance, a regression-based model where the dependent variable can take only two values. Within the context of the systems and methods described in the present disclosure, the probit function may be built using dependent variables that are associated with user preferences on control parameter settings. For instance, the user preferences could be a user's preferred choice between two different control parameter settings. The preference could be a forced choice (e.g., better/worse), or better/same/worse, or much better/better/worse/much worse, or so on.

The user's specific trade-off between exploration and exploitation can also be incorporated into the Bayesian optimization. For instance, some users may be more willing to try more therapy and thus that user's tolerance for exploitation versus exploration may be different from other users.

Implementing user preference to design the control parameter settings for the controllable medical device effectively amounts to a changing cost function over time. The methods described in the present disclosure are capable of optimizing this changing cost function to select the settings that are contained within the current set of user preferences.

Figure 3A:
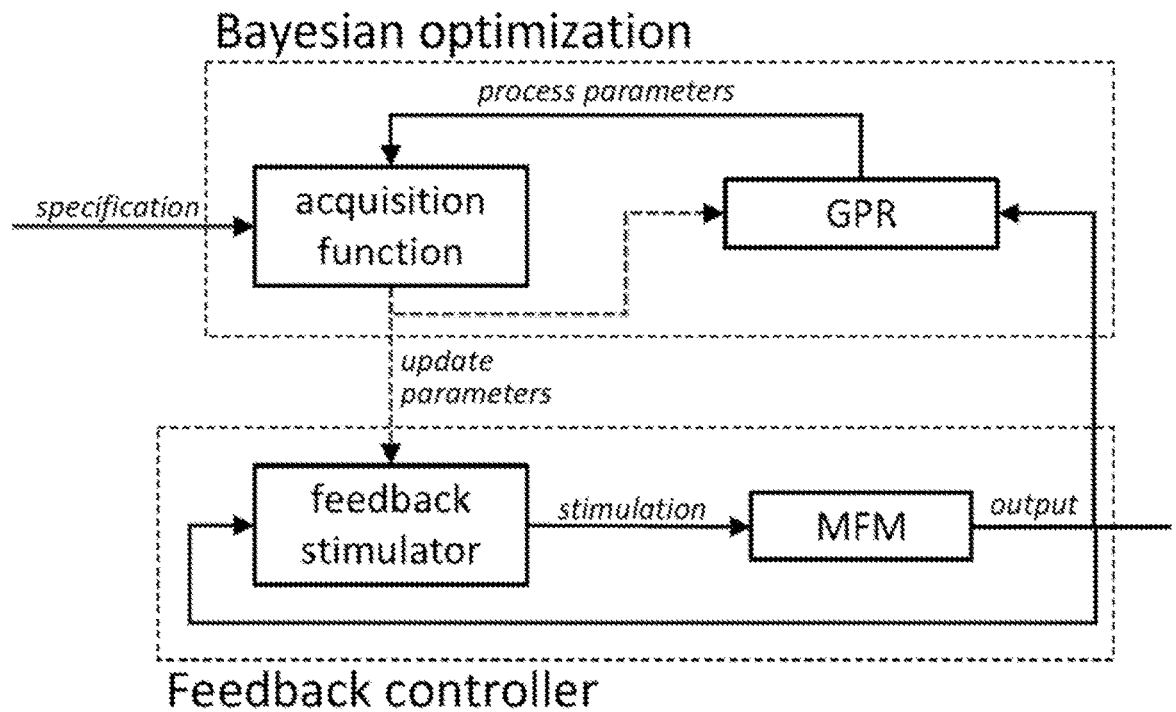
FIG. 3A is a block diagram of an example adaptive dual controller that implements a feedback controller and a Bayesian optimization loop for controlling a controllable medical device, such as an electrical stimulation device.

In an example study, the adaptive controller described in the present disclosure was tested for controlling a neurostimulator used in a DBS application. In this example, an adaptive dual controller ("ADC") was implemented using a hardware processor and memory. The ADC generally included an inner loop and an outer loop, as shown in the example configurations in FIGS. 3A and 3B. The inner loop was a parameterized feedback control loop, and the outer loop was a parameter adjustment loop that implemented the Bayesian optimization described in the present disclosure.

Figure 4:
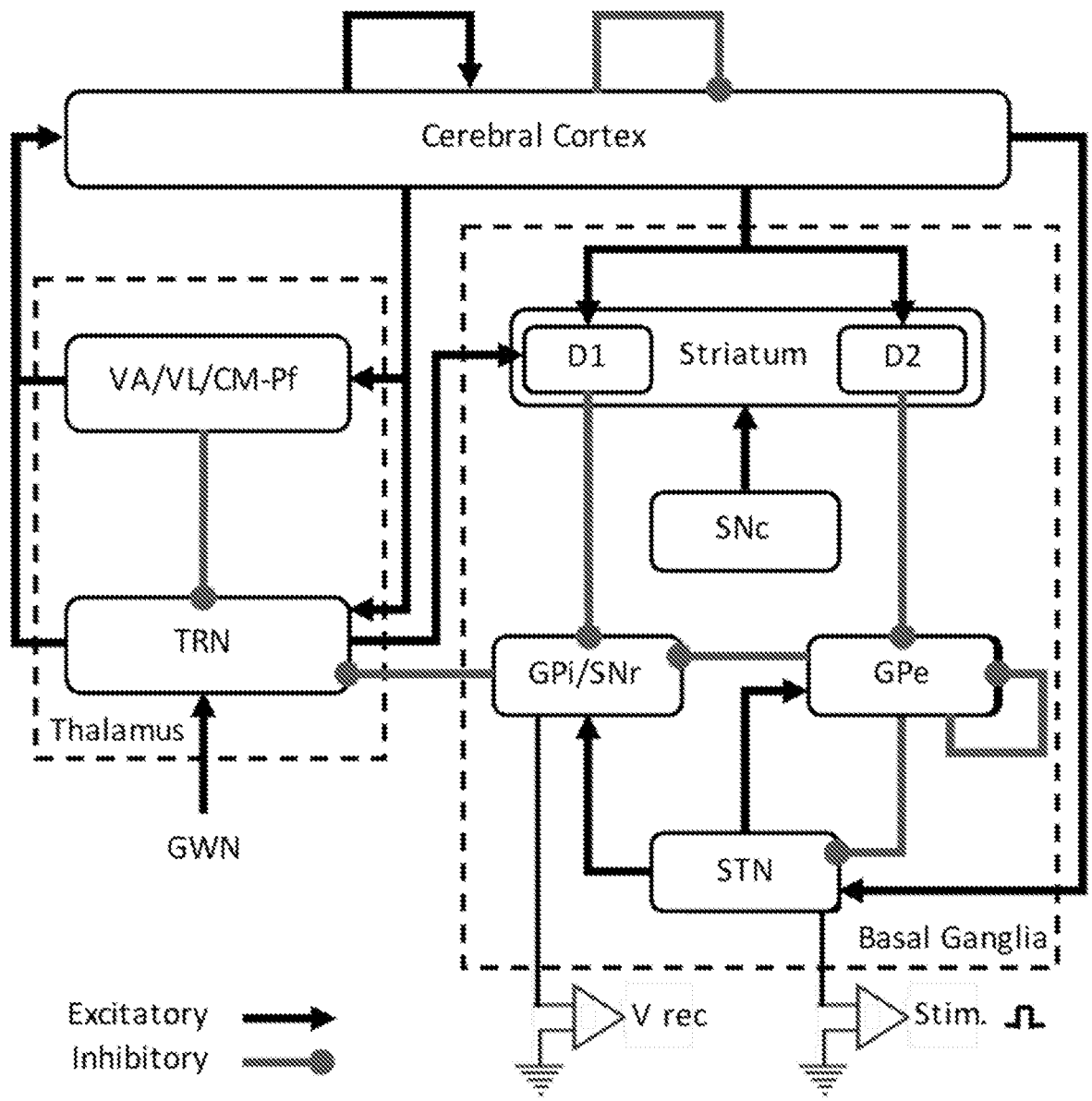
FIG. 4 shows the structure of an example BGTCs mean field model. Black arrows represent excitatory connections, red circles represent inhibitory connections. Simulated DBS is applied to the STN, and local field potentials (LFPs) are recorded from the GPi.

In this example, the inner loop of the ADC included a closed-loop feedback stimulator. The inner loop received information from a model that was based on a local field potential ("LFP") of the GPi, as shown in FIG. 4. The model shown in FIG. 4 is a physiologically realistic mean-field model ("MFM") of the basalganglia thalamocortical system ("BGTCs"). The BGTCs MFM models the mean firing rate and voltage of nine cortical and subcortical structures using two second-order differential equations.

DBS was added to the model by representing a DBS pulse as a direct current injection into the target structure. Integrating Ohm's law for capacitors results in the following:

$$\Delta V = \frac{\Delta t \cdot i}{C}. \quad (7)$$

Figure 5A:
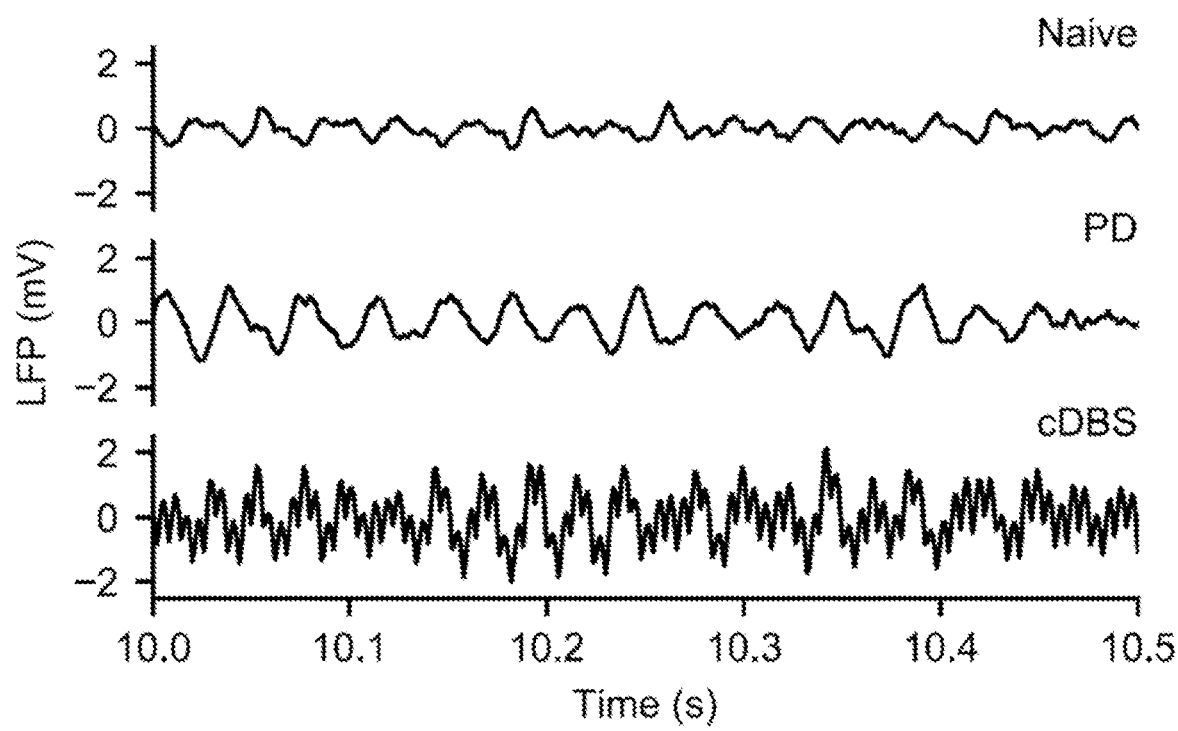
FIGS. 5A and 5B show example model results. (a) time-series data in three conditions: nave, PD, and PD with cDBS. (b) PSD comparing nave to PD, and PD to DBS. The model naturally produces a peak at 28 Hz, which is increased and widened in the Parkinsonian state. When DBS is applied to the model, the amplitude of the 28 Hz oscillation decreases.
Figure 5B:
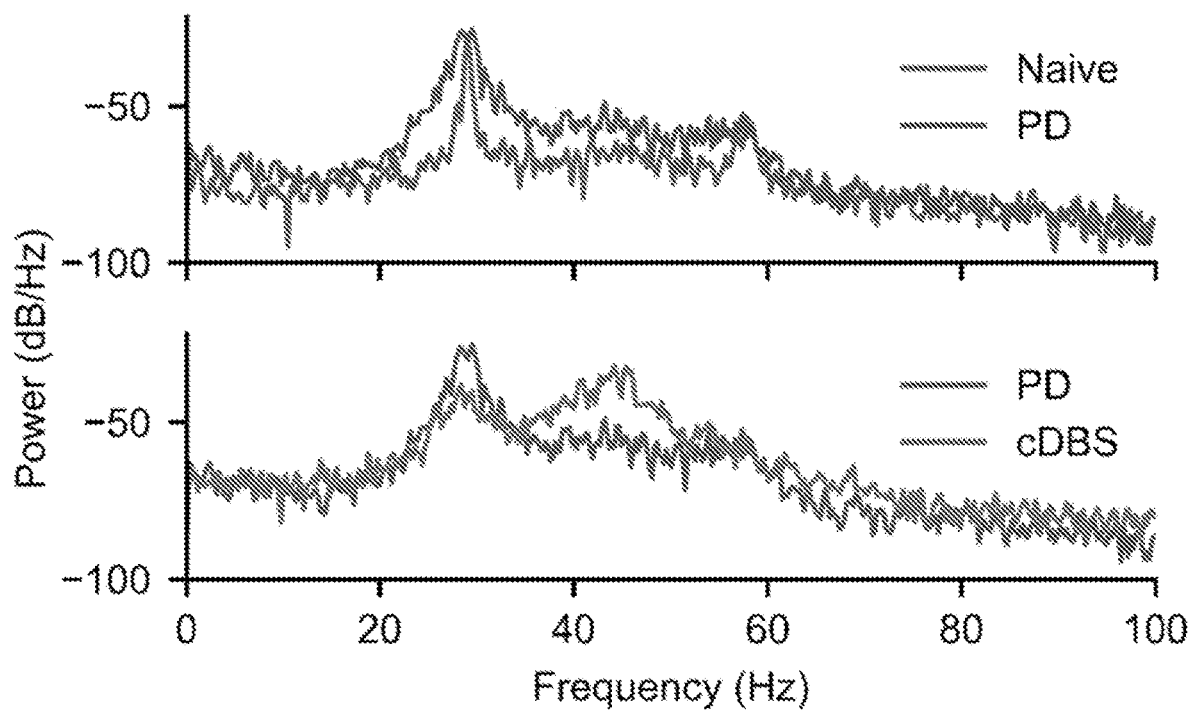

DBS was therefore modeled by directly adding the total charge of a monophasic DBS pulse (divided by the membrane capacitance) to the first derivative of the voltage. FIG. 5 shows example voltage traces from the GPi in the nave, PD, and PD with DBS states, as well as power spectrum from each trace.

Referring again to FIG. 3A, the inner loop extracts phase and amplitude information from the LFP in real time. In some embodiments, then, the inner loop has three parameters: an oscillation phase threshold, an oscillation amplitude threshold, and a stimulus amplitude. In other embodiments, different parameters can be extracted and thus the inner loop can have different parameters. In general, the inner loop operated on a short timescale, such as 1 ms.

Figure 3B:
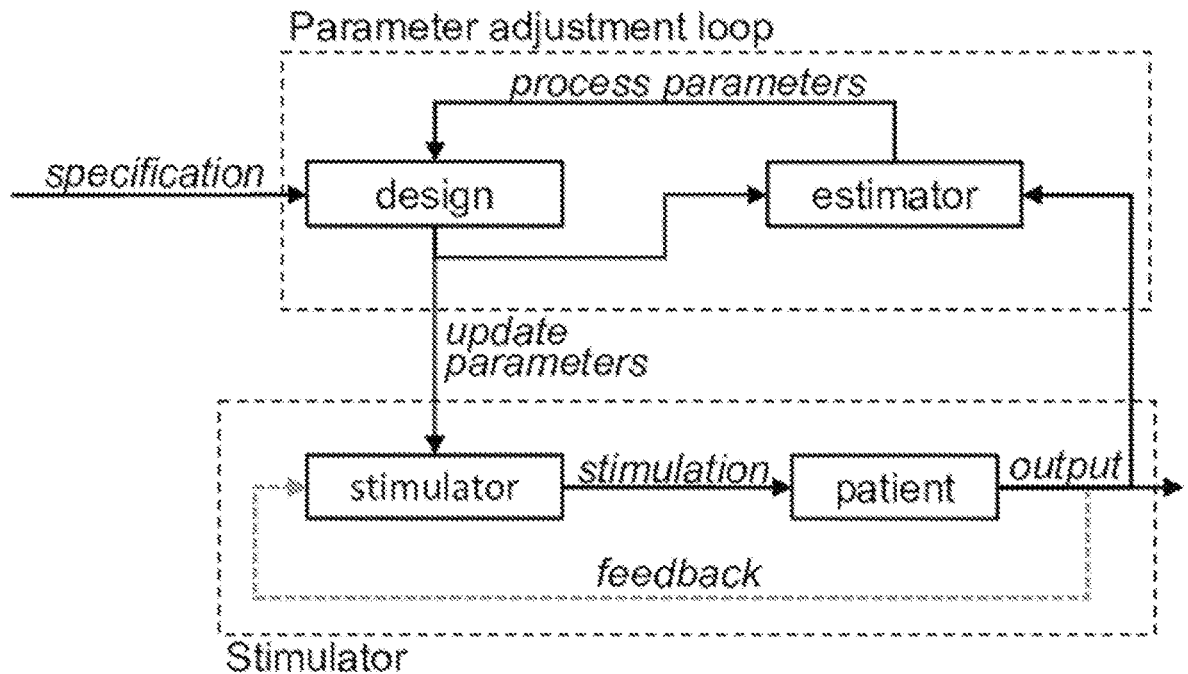
FIG. 3B is a block diagram of an example adaptive dual control that implements a feedback controller and a Bayesian optimization loop for controlling a controllable medical device, such as an electrical stimulation device.

As shown in the example in FIG. 3B, the adaptive dual controller can be configured to have dual goals (exploitation and exploration), and can be composed of two loops: an inner parameterized stimulator and an outer parameter adjustment loop. The inner loop may incorporate feedback from the user to alter stimulation. The outer loop is composed of an estimator and a design block, and is given a specification. The estimator builds a model of the relationship between stimulation parameters and some measure of user outcome, which it passes on to the design block. The design block then incorporates this information with the specification to select new parameters for the inner loop. The inner loop operates on a much shorter timescale than the outer loop.

Figure 6:
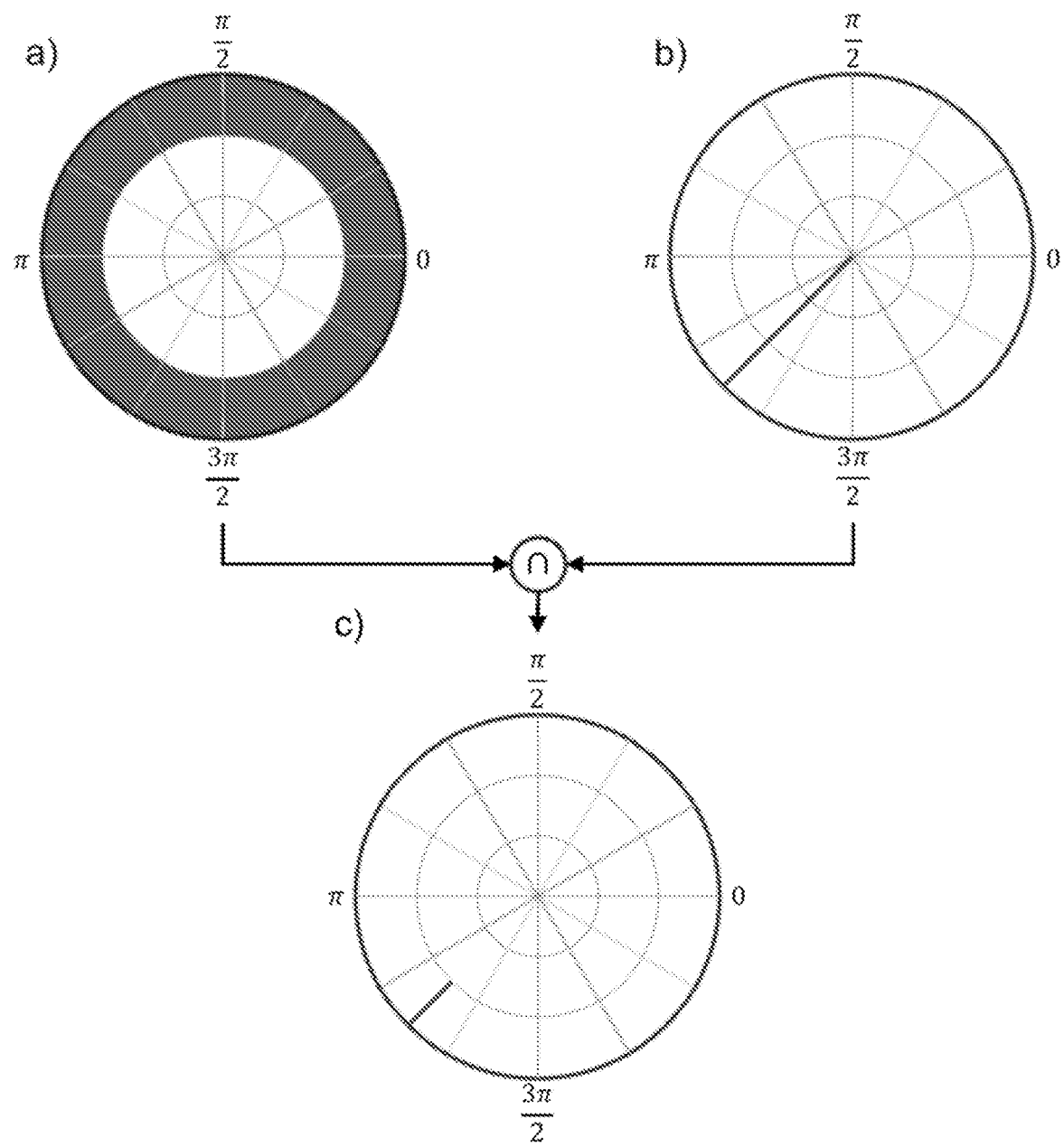
FIG. 6 shows a graphical illustration of (a) amplitude feedback stimulation, (b) phase feedback stimulation, and (c) combined phase/amplitude feedback stimulation strategies. In each figure, the red region indicates regions of the state space in which the controller delivers stimulation.

To implement phase and amplitude feedback stimulation, a real-time method of accurately estimating both phase and amplitude of an oscillation can be used. As one example, phasic stimulation has been accomplished by band-pass filtering the signal and then using the time since the preceding zero crossing. Amplitude-based stimulation has been achieved by rectifying and smoothing the band-passed signal for 400 ms. A visualization of amplitude feedback stimulation, phase feedback stimulation, and combined phased/amplitude feedback stimulation is shown in FIG. 6.

As another example, a sliding Fourier transform technique referred to as the Sliding Windowed Infinite Fourier Transform ("SWIFT") and described in co-pending U.S. Provisional Patent Appln. No. 62/520,265, which is herein incorporated by reference in its entirety, can be used. Unlike other methods of phase/amplitude estimation, the SWIFT technique directly and efficiently calculates the windowed Fourier transform of the signal, centered on $\omega=2\pi f/f_s$ and windowed with an infinite length, causal exponential window. In a variation referred to as αSWIFT, the α function window, which is the difference between two exponentials with different time constants, is used to achieve improved frequency resolution.

Figure 7:
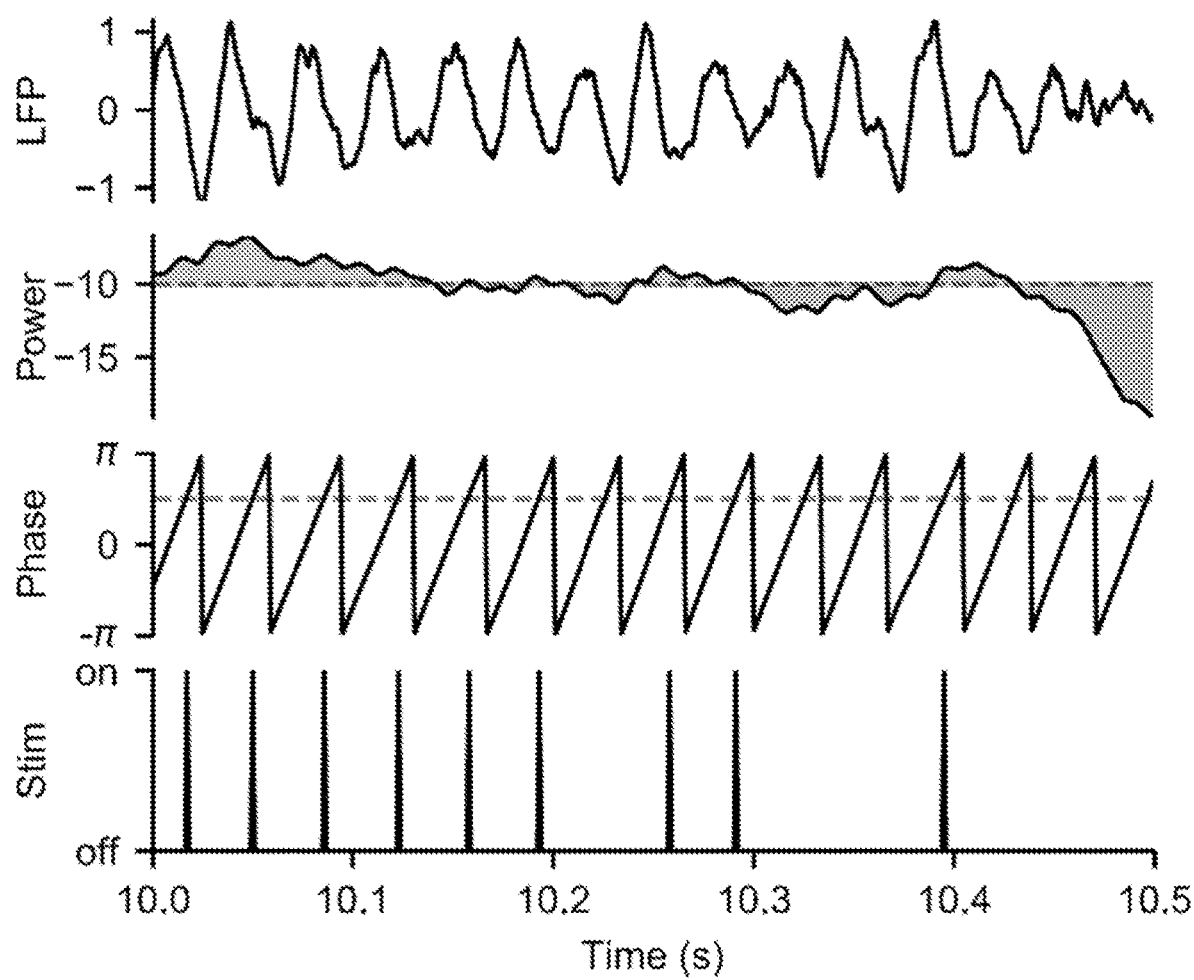
FIG. 7 shows phase/amplitude feedback stimulation algorithm operating on an example LFP. Top: Simulated LFP recorded from the STN of the MFM. Middle: Power and phase calculated from the LFP using the αSWIFT algorithm. The dotted lines indicate the power and phase thresholds for stimulation. Bottom: Stimulation is triggered when the phase crosses the phase threshold, but only if the power is above the power threshold.
Figure 8:
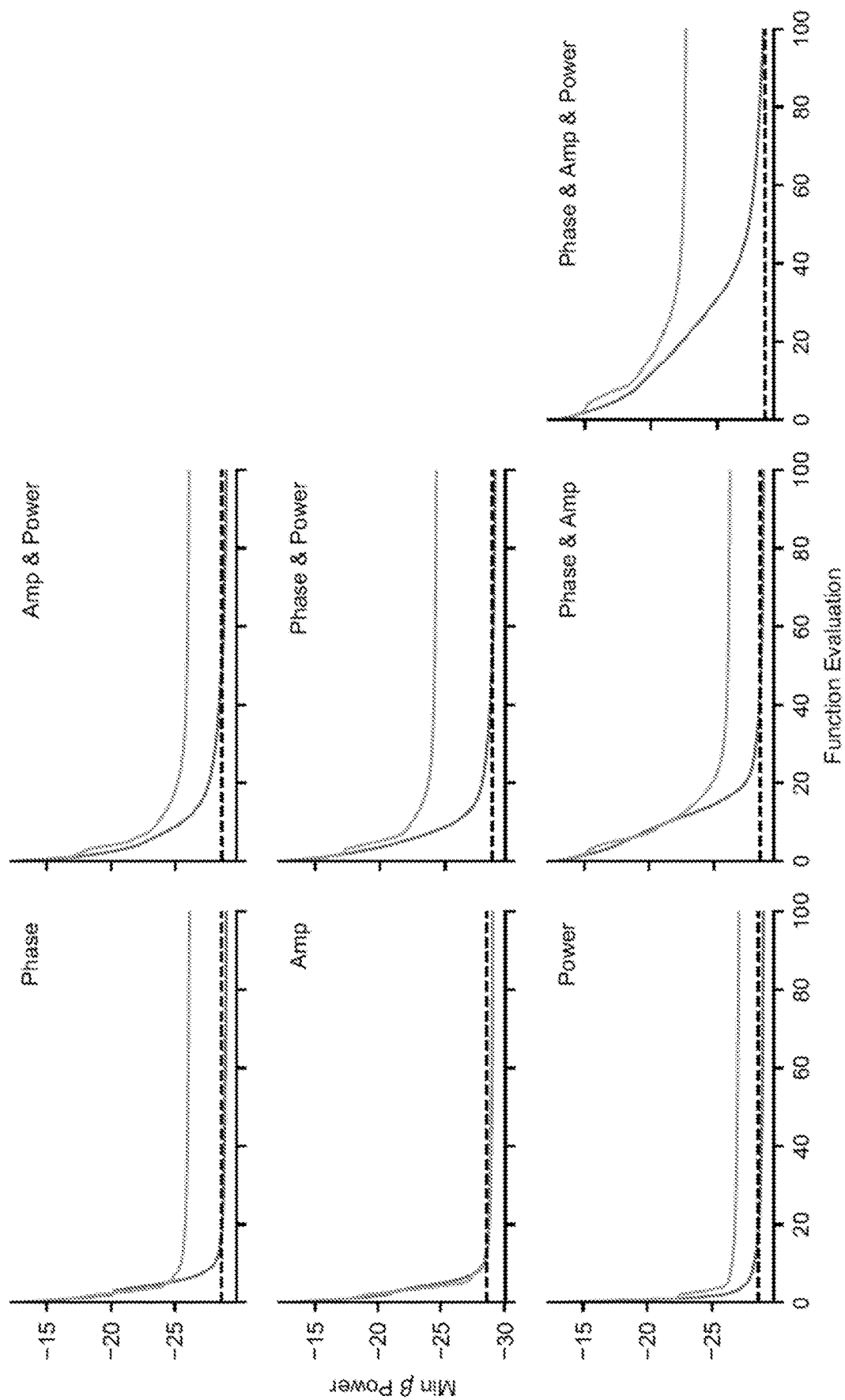
FIG. 8 shows examples of Bayesian optimization working on the model and shows how it performs relative to brute force optimization and Nelder-Mead.

The SWIFT algorithm has two parameters that control its behavior: the center frequency, $\omega$; and the time constant, $\tau$. For the αSWIFT algorithm two time constants are used: $\tau_{slow}$ and $\tau_{fast}$. The center frequency, $\omega$, can be set to match frequency information of the model. For instance, the center frequency can be set to match the center frequency of a beta peak in the model. The $\tau$ time constant ($\tau_{slow}$ in αSWIFT) controls the time-frequency tradeoff: a shorter time constant leads to higher temporal resolution, but lower frequency resolution (i.e., wider frequency response). As one example of tuning this tradeoff, the width of the SWIFT algorithm's frequency response can be matched to the width of the model's beta peak at −6 dB (or 50% power reduction). FIG. 7 shows an example of the phase amplitude feedback stimulation algorithm operating on an example LFP, in which stimulation is triggered off both phase and amplitude. FIG. 8 shows a comparison of the Bayesian optimization described in the present disclosure working on the model used in this example, and shows how the Bayesian optimization (blue lines) performs relative to brute force optimization and Nelder-Mead (orange lines).

Figure 9A:
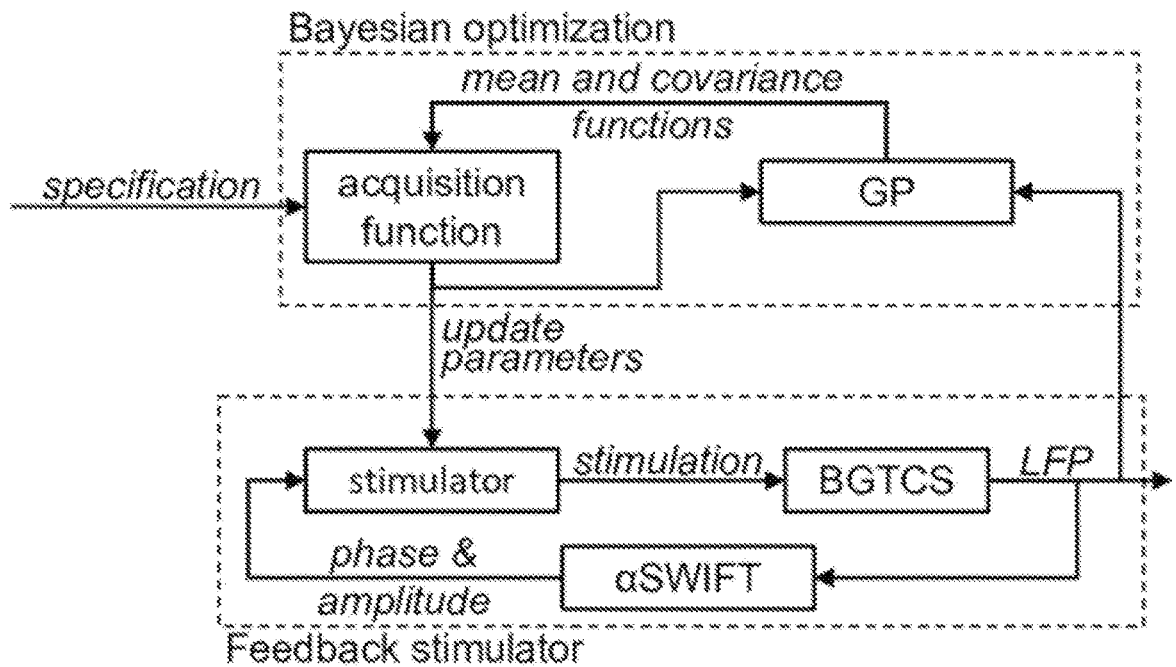
FIG. 9A is another example block diagram of an adaptive dual controller.
Figure 9B:
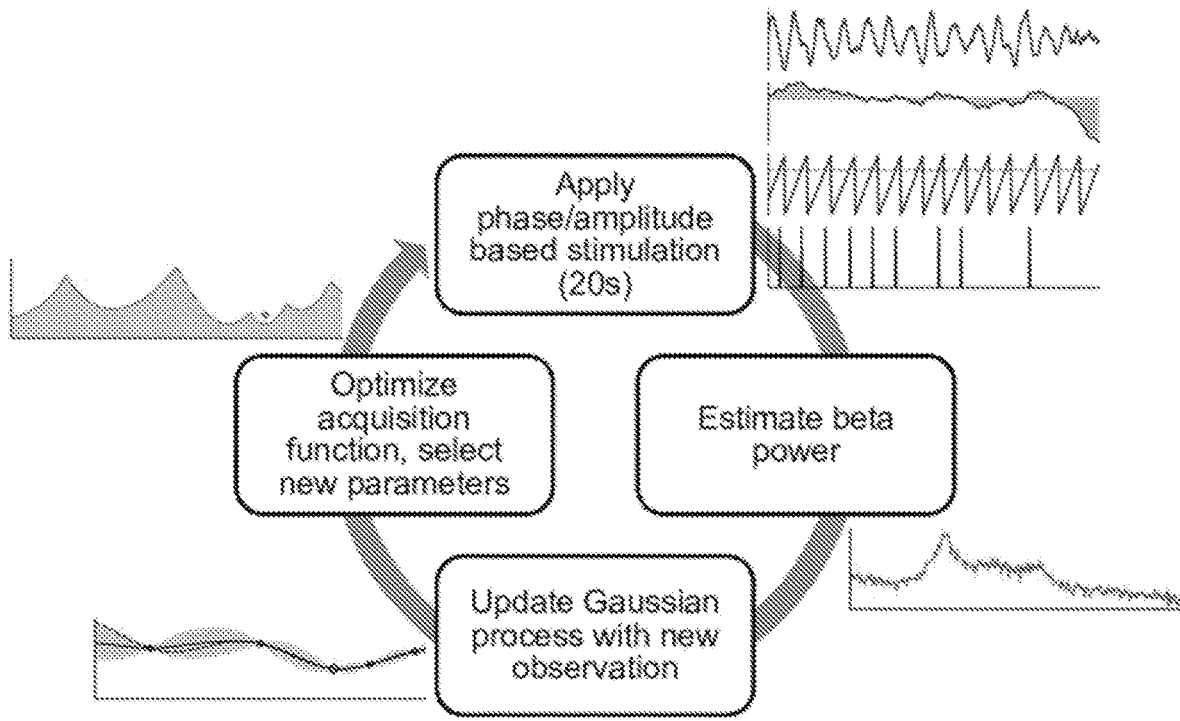
FIG. 9B is an illustrative example showing an overview of the cyclic operation of the adaptive dual controller of FIG. 9A.

FIGS. 9A-9B show another example of a Bayesian adaptive dual controller. FIG. 9A shows an example of the Bayesian ADC control diagram. In this example, the Bayesian ADC's inner loop was composed of a phase/power based feedback stimulator. The outer Bayesian optimization loop was composed of a Gaussian process (GP), and acquisition function. The Gaussian process builds a model of how the stimulation parameters affect the feedback signal, and the acquisition function uses this information to select the next parameter set. FIG. 9B shows an overview of the Bayesian ADC's cyclic operation. The Bayesian ADC sets the stimulator parameters and applies phase/power based stimulation to the BGTCS for 20 s. It then estimates the effect of those parameters on beta power, and updates its GP with the new observation. Finally, it optimizes its acquisition function, and selects the next parameter set.

Figure 10:
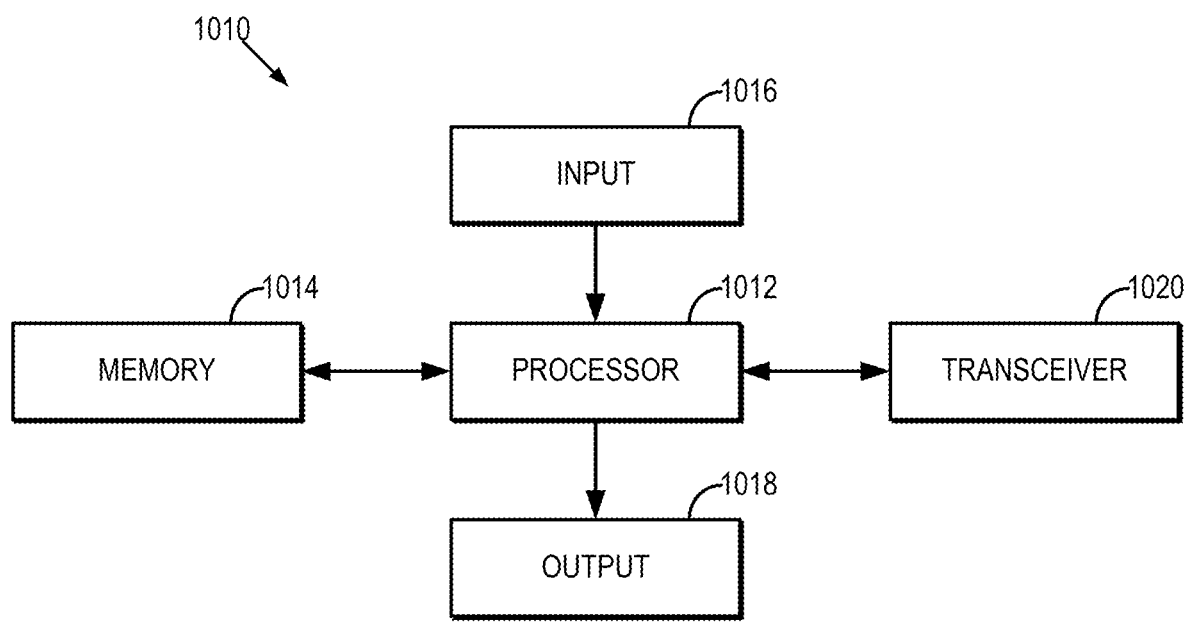
FIG. 10 is a block diagram of an example closed-loop stimulation system that can implement the methods described in the present disclosure.

Referring now to FIG. 10, an example of a controller 1010 that can implement the methods described in the present disclosure to adaptively control a controllable medical device is illustrated. In general, the controller 1010 includes a processor 1012, a memory 1014, and input 1016, and an output 1018. The controller 1010 can be implemented as part of a controllable medical device, or as a separate controller that is in communication with the controllable medical device via the output 1018. As one example, the controller 1010 can be implemented in a controllable medical device, such as an implantable medical device (e.g., an implanted nerve stimulation system or an implanted cardiac rhythm management system), a hearing aid, and so on. In other examples, the controller 1010 can be implemented in a remote computer that communicates with the controllable medical device. In still other example, the controller 1010 can be implemented in a smartphone that is paired with the controllable medical device, such as via Bluetooth or another wireless or wired communication.

In some embodiments, the input 1016 is capable of sensing feedback data from the user. As one example, the feedback data can be electrophysiological activity, and the input 1016 can be one or more electrodes. As another example, the feedback data can be chemical signal data, such as measured levels of chemicals. In such instances, the input 1016 can include a suitable sensor for measuring the chemical signal data. As noted above, such a sensor could be a part of the controllable medical device, or could be a separate sensor that is in communication with the controller 1010 via the input 1016, whether through a wired or wireless connection. Such chemical data could also be measured through other means, such as via a blood sample taken from the user, and transmitted to the controller 1010 via the input 1016. The input 1016 can thus more generally include a wired or wireless connector for receiving feedback data, which as noted above may also include behavioral or user preference data. In these latter examples, the feedback data can include a response surface generated from the behavioral or user preference data, such as a probit function, that is transmitted to the controller 1010 via the input 1016.

The processor 1012 includes at least one hardware processor to execute instructions embedded in or otherwise stored on the memory 1014 to implement the methods described in the present disclosure. The memory can also store measured feedback data for processing, as well as settings to be provided to the processor 1012 for generating control signals to be provided to a controllable medical device via the output 1018. As described above, these settings can be stored and also updated by the adaptive control implemented by the controller 1010.

The output 1018 communicates control signal to a controllable medical device. As one example, where the controllable medical device is an electrical stimulation device, the control signals provided to the output 1018 can control one or more electrodes to operate under control of the controller 1010 to sense electrophysiological activity in a subject and to deliver electrical stimulations to the subject in response thereto. Sensing circuitry in the controller 1010 can detect and processes electrophysiological activity sensed by the one or more one electrodes via the input 1016 to determine the optimized stimulation settings (e.g., phasic burst stimulation settings) based on the methods and algorithms described above. The optimized settings are provided as instructions to a pulse generator in the electrical stimulation device via the output 1018, which in response to the instructions provides an electrical signal to the one or more electrodes to deliver the electrical stimulations to the subject.

The controller 1010 can also include a transceiver 1020 and associated circuitry for communicating with a programmer or other external or internal device. As one example, the transceiver 1020 can include a telemetry coil. In some embodiments, the transceiver 1020 can be a part of the input 1016.

In operation, the controller 1010 receives feedback data from the subject via the input 1016. These feedback data are provided to the processor 1012 where they are processed. For example, the processor 1012 analyzes the feedback data and generates an appropriate response surface, or otherwise generates a GPR to be used for the Bayesian optimization to update the control parameter settings for the controllable medical device.

In one non-limiting example, the processor 1012 can process electrophysiological signal data to estimate biomarkers such as amplitude data, phase data, or both, from the measured data. In these instances, the processor 1012 can analyze the electrophysiological signals using a SWIFT or αSWIFT algorithm to extract the relevant amplitude and phase data. In other example, other biomarkers can be extracted or estimated from the electrophysiological signals, such as phase-amplitude coupling, evoked compound action potentials, or other parameters or characteristics that can be extracted or estimated from the electrophysiological signals. The extracted biomarkers are then input to a Bayesian optimization algorithm implemented by a hardware processor and memory 1014 of the controller 1012 to determine optimized settings for the delivery of electrical stimulation to the subject, as described above in detail. The optimized settings are provided to the electrical stimulation device via the output 1018 to control one or more electrodes to generate electrical stimulation that will achieve the desired effect in the subject, such as preventing an anticipated pathological electrophysiological event.

The present disclosure has described one or more preferred embodiments, and it should be appreciated that many equivalents, alternatives, variations, and modifications, aside from those expressly stated, are possible and within the scope of the invention.

The invention claimed is:

1. An adaptive controller for controlling a controllable medical device, comprising:
   an input that receives feedback data representative of a treatment response or effect in a subject;
   a processor in communication with the input and programmed to:
     receive the feedback data from the input and generate a posterior distribution therefrom;
     estimate an acquisition function from the posterior distribution; and
     generate updated control parameter settings based on the acquisition function;
   a memory in communication with the input and the processor, wherein the memory stores instructions for generating updated control parameter settings, the feedback data received from the input, and the updated control parameter settings generated by the processor;
   an output that communicates the updated control parameter settings to a controllable medical device comprising an electrical stimulation device having a pulse generator and at least one electrode in communication with the pulse generator;
   wherein the processor is programmed to generate a response surface based on the feedback data using a probit function;
   wherein the feedback data comprise user preferences between two different control parameter settings;
   wherein the posterior distribution is generated using the response surface generated based on the feedback data using the probit function; and
   wherein the processor receives control signals generated based on the updated control parameters settings and sends the controls signals to the pulse generator of the controllable medical device by the output; and wherein the pulse generator of the controllable medical device receives the control signals from the output and in response thereto generates electrical signals and sends the electrical signals to the at least one electrode of the controllable medical device to generate an electrical stimulation based on the updated control parameter settings.

2. The adaptive controller as recited in claim 1, wherein the feedback data received from the input further comprise behavior metrics, and wherein the processor is programmed to also generate the response surface based on the behavior metrics.

3. The adaptive controller as recited in claim 1, wherein the feedback data received from the input further comprise at least one of physiological data or behavioral metrics.

4. The adaptive controller as recited in claim 3, wherein the physiological data comprises at least one of neural signals, cardiac signals, or chemical signals.

5. The adaptive controller as recited in claim 4, wherein the physiological data comprises chemical signals including at least one of insulin levels or glucose levels.

6. The adaptive controller as recited in claim 1, wherein the user preferences comprise user preference responses to a questionnaire.

7. The adaptive controller as recited in claim 1, wherein the electrical stimulation device comprises at least one of a peripheral nerve stimulator, a central nervous system stimulator, a cardiac pacemaker, or a cardiac resynchronization therapy (CRT) device.

8. A system, comprising:
  a controllable medical device comprising an electrical stimulation device having a pulse generator and at least one electrode in communication with the pulse generator and in contact with a subject to deliver electrical stimulation according to control parameter settings to the subject patient; and
  a controller, the controller comprising:
    (i) an input that receives feedback data representative of a treatment response or effect in the subject patient of delivered electrical stimulation, wherein the feedback data comprises user preference relative to electrical stimulation delivered according to a first control parameter setting and different electrical stimulation delivered according to a second control parameter setting;
    (ii) a processor in communication with the input and programmed to:
      (A) receive the feedback data from the input;
      (B) generate a response surface based on the feedback data using a probit function;
      (C) generate a posterior distribution from the response surface;
      (D) estimate an acquisition function from the posterior distribution; and
      (E) generate updated control parameter settings based on the acquisition function;
    (iii) a memory in communication with the input and the processor, wherein the memory stores instructions for receiving the feedback, generating the response surface, generating the posterior distribution, estimating the acquisition function, generating updated control parameter settings and storing control parameter settings and updated control parameter settings;
    (iv) an output that communicates the updated control parameter settings to the controllable medical device;
  wherein the controllable medical device receives the updated control parameters settings, and the pulse generator delivers electrical stimulation to the subject patient according to the updated control parameter settings.

* * * * *